United States Patent
Leasko

(10) Patent No.: US 6,203,767 B1
(45) Date of Patent: Mar. 20, 2001

(54) PERACETIC ACID CARD READER AND CARD STYLE SENSOR

(75) Inventor: Lawrence W. Leasko, Perry, OH (US)

(73) Assignee: Steris Corporation, Mentor, OH (US)

( * ) Notice: Subject to any disclaimer, the term of this patent is extended or adjusted under 35 U.S.C. 154(b) by 0 days.

(21) Appl. No.: 09/187,908

(22) Filed: Nov. 6, 1998

(51) Int. Cl.$^7$ ................... A01N 2/00; A61L 9/00; A61L 2/00

(52) U.S. Cl. ............... 422/292; 422/28; 436/150; 436/55

(58) Field of Search ................... 422/292, 105, 422/107, 108, 116, 3, 62, 82.02; 436/129, 135, 150, 151, 55

(56) References Cited

U.S. PATENT DOCUMENTS

| | | |
|---|---|---|
| 2,794,869 | 6/1957 | Noregaard . |
| 3,902,970 | 9/1975 | Levin . |
| 4,016,308 | 4/1977 | Frazee . |
| 4,231,458 | 11/1980 | Limone et al. . |
| 4,447,399 * | 5/1984 | Runnells ............... 422/113 |
| 4,680,271 | 7/1987 | Williams . |
| 4,871,053 | 10/1989 | Cosgrave et al. . |
| 4,892,706 * | 1/1990 | Kralovic et al. ............ 422/28 |
| 5,037,623 | 8/1991 | Schneider et al. . |
| 5,091,343 | 2/1992 | Schneider et al. . |
| 5,116,575 | 5/1992 | Badertscher et al. . |
| 5,126,034 | 6/1992 | Carter et al. . |
| 5,217,698 | 6/1993 | Siegel et al. . |
| 5,225,160 | 7/1993 | Sanford et al. . |
| 5,279,799 * | 1/1994 | Moser ............... 422/292 |
| 5,374,892 | 12/1994 | Sturrock et al. . |
| 5,382,331 | 1/1995 | Banks . |
| 5,395,493 | 3/1995 | Pinkowski . |
| 5,400,818 | 3/1995 | Cosentino et al. . |
| 5,439,654 | 8/1995 | Kochte . |
| 5,470,484 | 11/1995 | McNeel . |
| 5,494,637 * | 2/1996 | Barlow ............... 422/28 |
| 5,503,720 | 4/1996 | Teske . |
| 5,552,115 | 9/1996 | Malchesky . |
| 5,644,501 | 7/1997 | Lin et al. . |
| 5,647,391 | 7/1997 | Chan et al. . |
| 5,759,490 | 6/1998 | Malchesky . |
| 5,761,069 * | 6/1998 | Weber et al. ............ 364/478.01 |

FOREIGN PATENT DOCUMENTS

WO 97/08544   3/1997   (WO) .

* cited by examiner

Primary Examiner—Terrence R. Till
Assistant Examiner—Monzer R. Chorbaj
(74) Attorney, Agent, or Firm—Fay, Sharpe, Fagan, Minnich & McKee, LLP

(57) ABSTRACT

A disposable sensor card (74) includes a polymeric substrate (80), such as polyester, printed with a plurality of electrodes (78), and a reuse-prevention system (150) which includes a fuse link (152) and a cut link (154). A controller (70) tests the fuse link and cut link to see if they have been destroyed. If the controller determines that the two links are good, a sensor card support system (72), which includes a ram (130), clamps the sensor card over an opening in a manifold (138) so that the electrodes are in contact with a decontaminant solution, such as peracetic acid solution, passing through the manifold. The controller detects an electrical property of the electrodes and determines a concentration of the decontaminant therefrom. During the clamping process, a cutter (170) severs the cut link. A memory of the cut link is retained by the controller. If power to the controller is interrupted, the memory is lost and the controller detects that the cut link is broken when power is regained. At the end of a decontamination process, the controller switches to a "power off" mode and detects that the cut link is severed. When the controller detects that the cut link is severed, the controller blows the fuse link and the sensor card support system unclamps the sensor card. The severed cut link provides a visual indication that the card is spent.

22 Claims, 7 Drawing Sheets

PERACETIC ACID CARD READER AND CARD STYLE SENSOR

BACKGROUND OF THE INVENTION

The present invention relates to the sterilization and disinfection arts. It finds particular application in conjunction with the detection of peracetic acid concentrations in decontamination systems used for the sterilization or disinfection of medical and pharmaceutical equipment, and will be described with particular reference thereto. It should be appreciated, however, that the invention is also applicable to the detection of other oxidizable and reducible species in fluid flow systems.

Endoscopes and similar medical devices having tubes or lumens formed therethrough are being used on an ever increasing basis in the performance of medical procedures. The popularity of these devices has lead to the development of improved decontamination systems, both in terms of the speed of the decontamination process and in the effectiveness of the decontamination. High temperature steam sterilization tends to be destructive towards some of the components of the endoscopes. As a result, liquid sterilization processes have been investigated. Glutaraldehyde, a common liquid disinfectant, is generally effective for disinfection of medical instruments. However, the sterilization process generally takes from 10 to 12 hours, which is frequently too long in today's health care facilities. Another drawback with glutaraldehyde systems is that they sterilize without cleaning. That is, they leave non-living biological contaminants on the medical instruments. The contaminants, although sterile, can break down and liberate harmful toxins when the instruments are subsequently reused.

Recently, peracetic acid sterilization systems have proven effective for the sterilization of medical instruments. Due to its limited shelf life and shipping restrictions, the peracetic acid is often prepared as needed from a mixture of precursors. The peracetic acid precursors are typically mixed with water and other chemicals in the bath. U.S. Pat. No. 5,116,575 to Badertscher, et al. discloses a powdered antimicrobial composition comprising acetylsalicylic acid and sodium perborate. Inhibitors and surfactants are also included in the composition, to aid in cleaning and preventing corrosion of the metal parts of the instruments. The composition is mixed with water in a bath. Items to be sterilized or disinfected are immersed in the bath for a period sufficient to effect sterilization or disinfection. Decontaminated items are rinsed before use to remove traces of the acid and other cleaning chemicals.

To insure effective sterilization or disinfection within a preselected period of time, the concentration of peracetic acid is maintained above a selective minimum effective level, typically around 2300–2500 ppm for sterilization of medical instruments.

The bath sterilization procedures does however have disadvantages. Operator errors can contribute to unsatisfactory sterilization. Specifically, inaccuracy in mixing the components may result in levels of peracetic acid below the minimum level required for sterilization. Thorough cleaning of the instruments is not insured if the instruments are removed from the bath before a minimum exposure period is completed. Handling of the instruments between sterilization and rising stages may lead to recontamination of the instruments.

Recently, dedicated decontamination systems have been developed which sterilize and rinse the medical instruments in an enclosed, automated system. Peracetic acid, either generated in situ or diluted from a concentrate, is delivered to a sterilization vessel and circulated over the instruments to be sterilized. U.S. Pat. No. 5,217,698 to Siegel, et al. discloses an office size instrument sterilization system of this type. Instruments to be sterilized are inserted in a cassette and the sterilant fluid circulated through the cassette. After sterilization, the instruments remain in the cassette in a sterile condition until needed in the hospital. For decontamination of larger instruments, U.S. Pat. No. 5,225,160 to Sanford, et al. discloses a wheeled decontamination apparatus.

To insure that an accurate dose of the powdered sterilants is provided, it is preferable to contain the components in a cup which is opened within the sterilization system when needed. U.S. Pat. No. 5,439,654 discloses a cutter for opening a sterilant-containing cup.

The use of a measured dose of sterilants or precursors does not always guarantee adequate levels of peracetic acid. Peracetic acid precursors and concentrates can decompose over time. Thus, even when the dosage is accurately measured, the concentration for peracetic acid in the solution is not always assured. Further, the peracetic acid concentration may be reduced when the medical instruments are heavily contaminated with biological materials.

Methods have been developed for detection of peracetic acid, and other oxidizable and reducible species, in solution. Dippable papers, for example, are easy to use, but lack accuracy, particularly at concentrations suitable for sterilization or disinfection. Chemical titration methods provide a more accurate measure of peracetic acid in solution, but are time consuming to perform and are prone to operator errors. They do not provide the rapid detection needed for automated sterilization and disinfection systems.

Recently, a number of electrochemical techniques have been developed for detection of oxidizable or reducible chemical species, such as mixtures of peracetic acid and hydrogen peroxide. U.S. Pat. No. 5,400,818 to Consentino, et al. discloses such a sensor. The sensor measures the resistivity of the solution, which is dependent on both the peracetic acid and the hydrogen peroxide concentrations. European patent application EP 0333246 A to Unilever PLC, discloses an electrochemical sensor using an amperometric method, in which a fixed potential is maintained between the reference and the working electrode. The current at the working electrode is used to determine the concentration of peracetic acid. Other species present, however, influence the current flowing, and hence the accuracy of the results.

U.S. Pat. No. 5,503,720 to Teske discloses a process for the determination of reducible or oxidizable species, such as peracetic acid, in sewage waste. The process uses potentiostatic amperometry to detect peracetic acid concentrations. The technique, however, depends on the achievement of a steady state, which frequently takes several hours. Such a detection system is unsuited to a fairly short term sterilization process.

The electrode systems used in such detection systems are generally bulky devices which are both costly to manufacture and require careful preparation of the electrode surfaces prior to use. Prolonged exposure to the test solution tends to degrade the electrodes and thus recalibration is generally employed before each use. Inaccurate measurements result when recalibration is not carried out or the electrodes are not thoroughly cleaned.

Recently disposable electrodes have been developed for analytical assays in medical and biochemical samples. The electrodes are laid down as an ink onto a plastic card. Leads connect the electrodes to electrochemical monitoring equipment. Typically, a few drops of the solution placed on the electrode. However, there is generally no method of determining when the electrode has reached the end of its useful life and for preventing reuse of an electrode intended for a single use.

The present invention provides for a new disposable plastic sensor card for peracetic acid and associated reader and sterilization equipment which overcomes the above-referenced problems and others.

SUMMARY OF THE INVENTION

In accordance with one aspect of the present invention, a decontamination system for sterilizing or disinfecting instruments with a decontaminant solution is provided. The system includes a decontamination cabinet which defines a chamber for receiving the instruments to be decontaminated, a source of the decontaminant solution, and a fluid line fluidly connecting the source of the decontaminant solution with the chamber. A sensor card support system supports a disposable sensor card in fluid communication with the fluid line. The sensor card includes a plurality of electrodes and a reuse-prevention system. Further, the system includes a controller for detecting an electrical property of the electrodes and determining a concentration of a decontaminant in the decontaminant solution from the detected electrical property and for detecting whether the reuse-prevention system has been activated.

In accordance with another aspect of the present invention, a sensor system for detecting a concentration of a component of a liquid disposed in a liquid treatment system is provided. The system includes a sensor card support system for supporting a disposable sensor card in fluid communication with the liquid in the liquid treatment system. The sensor card includes a plurality of electrodes and a reuse-prevention system. A controller for establishing electrical contact with the electrodes electrically measures an electrical property of the electrodes which is dependent on the concentration of the component in the liquid. A reuse-prevention activation system activates the reuse-prevention system. A detector detects an activation of the reuse-prevention system.

In accordance with yet another aspect of the present invention, a method for preventing reuse of a disposal sensor card for detecting the concentration of a decontaminant in a decontaminant solution is provided. The sensor card includes a plurality of electrodes and a reuse-prevention system. The method includes determining whether the reuse-prevention system on the sensor card has been activated, and, if the reuse-prevention system has not been activated, clamping the sensor card such that the electrodes are in contact with the decontaminant solution. The method further includes sensing an electrical property of the electrodes which is dependent on the concentration of the decontaminant in the decontaminant solution and activating the reuse-prevention system.

One advantage of the present invention is that an effective concentration of decontaminant.

Another advantage of the present invention is that a peracetic acid decontamination cycle is halted or extended if an insufficient concentration of peracetic acid is detected.

Another advantage of the present invention is that a fresh sensor card is dictated for each decontamination cycle, ensuring accurate operation of the decontaminant detection system.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components and in various steps and arrangements of steps. The drawings are only for purposes of illustrating a preferred embodiment, and are not to be construed as limiting the invention.

DETAILED DESCRIPTION OF THE PREFERRED EMBODIMENT

A sensor system A is used to detect the concentration of a component of a liquid in a fluid flow path. In a preferred embodiment, the sensor system is used for detecting the concentration of a sterilant or disinfectant in an aqueous solution flowing through an automated peracetic acid sterilization or disinfection system for decontamination of medical instruments, such as endoscopes, and the like. It should be understood, however, that the sensor system is not limited to the detection of sterilants and disinfectants and that the detection of other oxidizable and reducible species in a variety of fluid systems is also contemplated.

Figure 1:
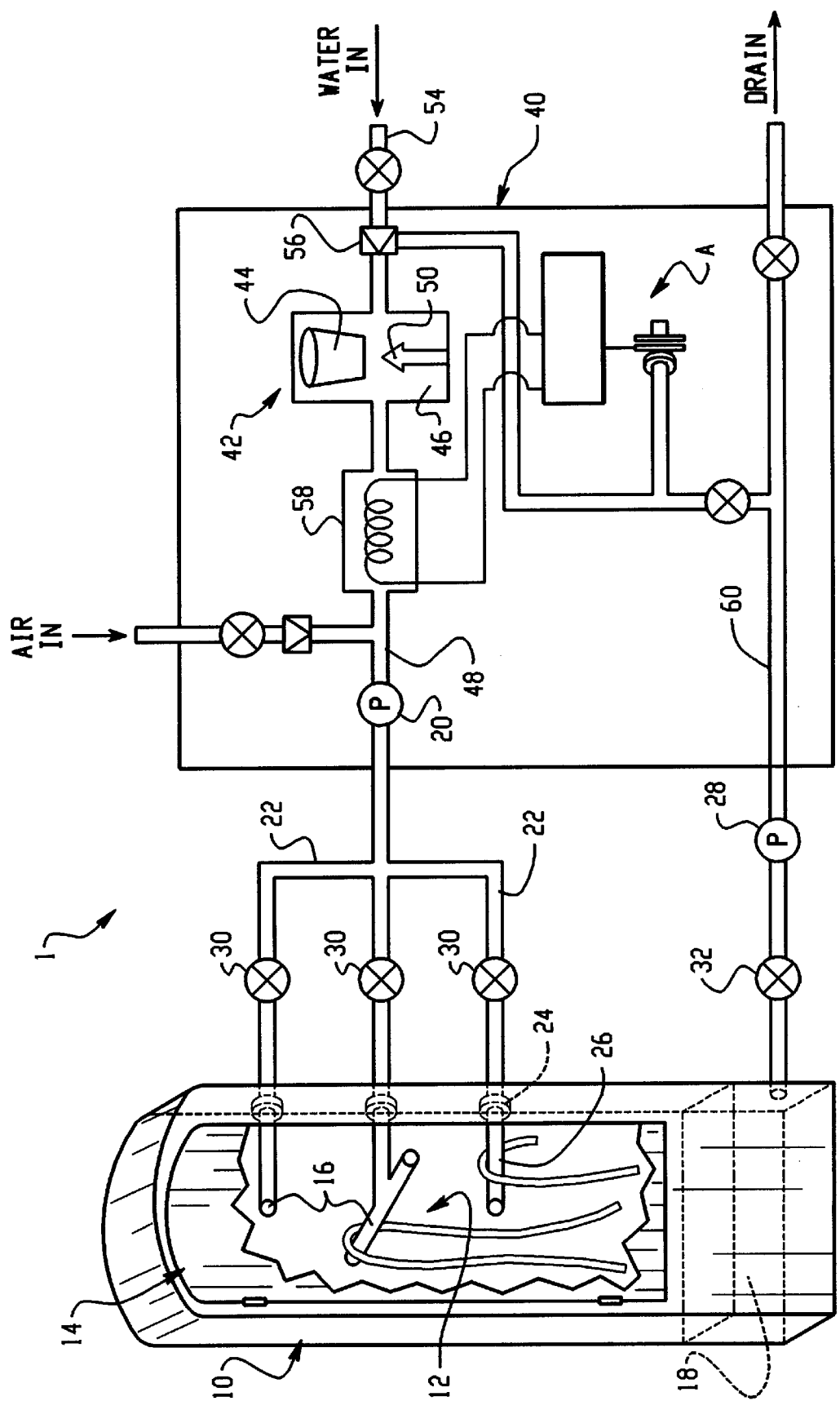
FIG. 1 is a schematic view of a decontamination system according to the present invention.

With reference to FIG. 1, an automated liquid decontamination system 1 for sterilization or disinfection of medical and pharmaceutical instruments, and the like, is shown. The system includes a decontamination cabinet 10 which defines a chamber 12. Items to be cleaned and sterilized or disinfected are loaded into the chamber through a door 14 in a wall of the decontamination cabinet. Nozzles 16, within the chamber, spray a liquid sterilant or disinfectant and other cleaning and rinsing liquids (herein jointly referred to as decontaminants) over the items. A collection tank or sump 18, at the base of the cabinet receives the sprayed decontaminant as it drips off the items.

A first pump 20 delivers the decontaminant under pressure to the nozzles 16 through fluid lines 22. Preferably, quick connect couplings 24 connect the fluid lines adjacent an exterior wall of the cabinet to interior fluid lines 26, within the chamber, so that the fluid lines can be uncoupled for removal of the cabinet from the rest of the system 1.

A second pump 28 withdraws the sprayed decontaminant from the tank 18 for reuse or disposal. Valves 30 and 32 control the flow of decontaminant into and out of the cabinet, respectively.

A supply cabinet 40, located adjacent the decontamination cabinet 10, houses a source 42 of the decontaminant and the sensor system A. The source 42 of the decontaminant preferably includes a disposable cup or other container 44 which holds a measured dose of concentrated decontaminant, in either liquid or solid form. A fresh cup is used for each decontamination cycle.

A well 46 receives the cup 44. The well is connected by a fluid line 48 to the pump 20. A cutter 50 cuts a wall of the cup to release the decontaminant when required. A water inlet line 54 delivers water to the well for mixing with the concentrated decontaminant to provide a dilute solution of the decontaminant. The water used may be tap water or treated water, such as distilled water. The quantity of water entering the system 1 is regulated to provide a decontaminant solution of a desired nominal concentration flowing through the chamber 12. The water is first passed through a microporous filter 56 which filters out particles of dirt and microorganisms.

Alternatively, the decontaminant is delivered in liquid form and metered from a bulk supply source (not shown). The liquid may be a concentrate, or diluted with water, ready for use.

A heater 58, disposed in fluid line 48 heats the decontaminant to a desired temperature for effective decontamination. The second pump 28 returns the sprayed decontaminant solution to chamber 12 via a return fluid line 60. The return fluid line preferably directs the returned decontaminant solution through the well 46 to insure thorough mixing and dissolution of the concentrated decontaminant.

The sensor system A measures the concentration of the decontaminant in the decontaminant solution flowing through the chamber 10. As shown in FIG. 1, the sensor system is disposed in the return fluid line 60, so that the concentration of the decontaminant solution is measured after contact with the instruments being decontaminated. It should be appreciated, however, that the sensor system is also conveniently disposed in any of the fluid flow lines 22, 26, 60 of the decontamination system, although greater initial fluctuations in concentration measurements are to be expected if the sensor is located between the well 46 and the chamber nozzles 16. These fluctuations are reduced, however, by allowing the decontaminant solution to circulate through the chamber one or more times before initiating sensing.

Figure 2:
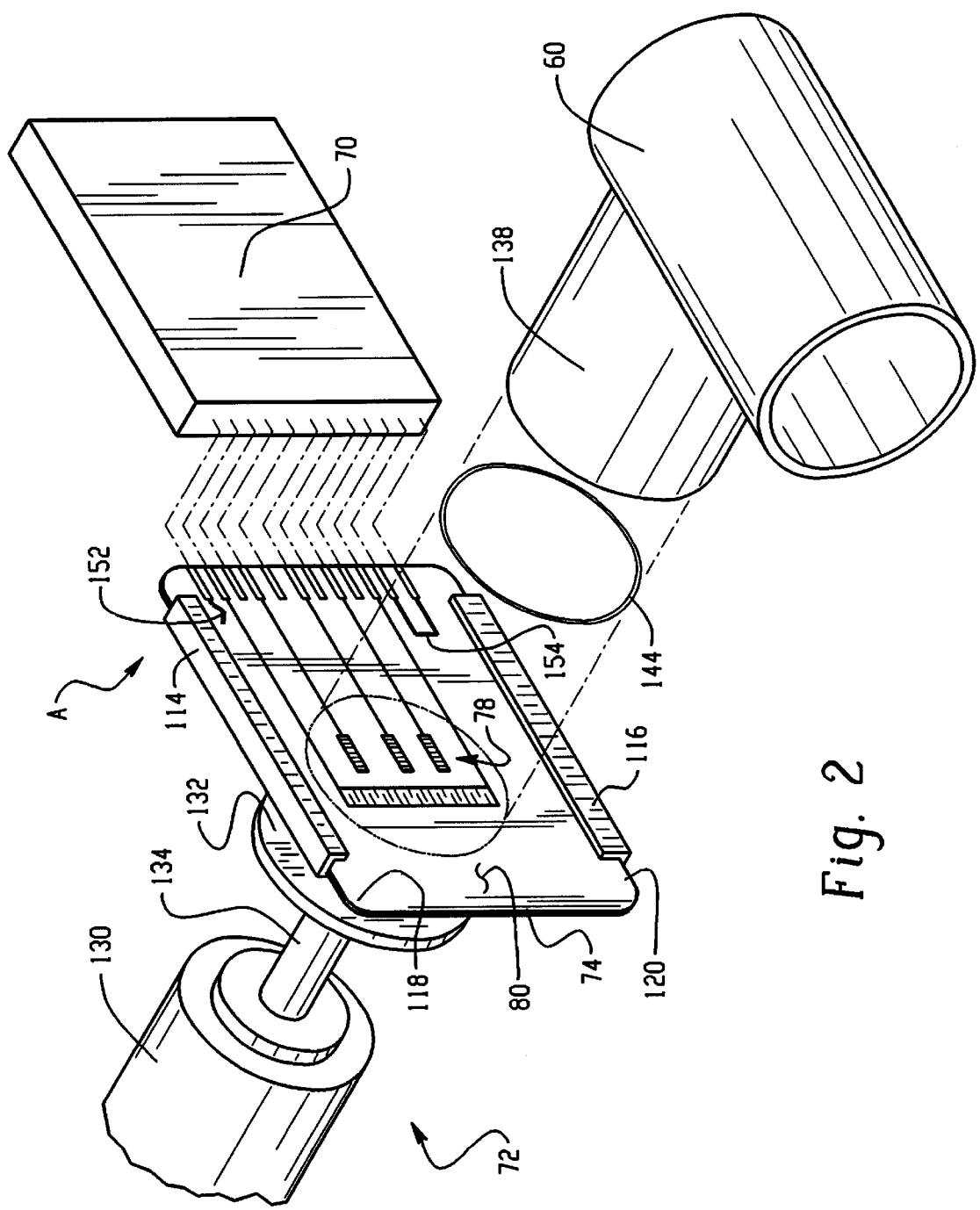
FIG. 2 is an enlarged perspective view of the sensor system of FIG. 1.
Figure 3:
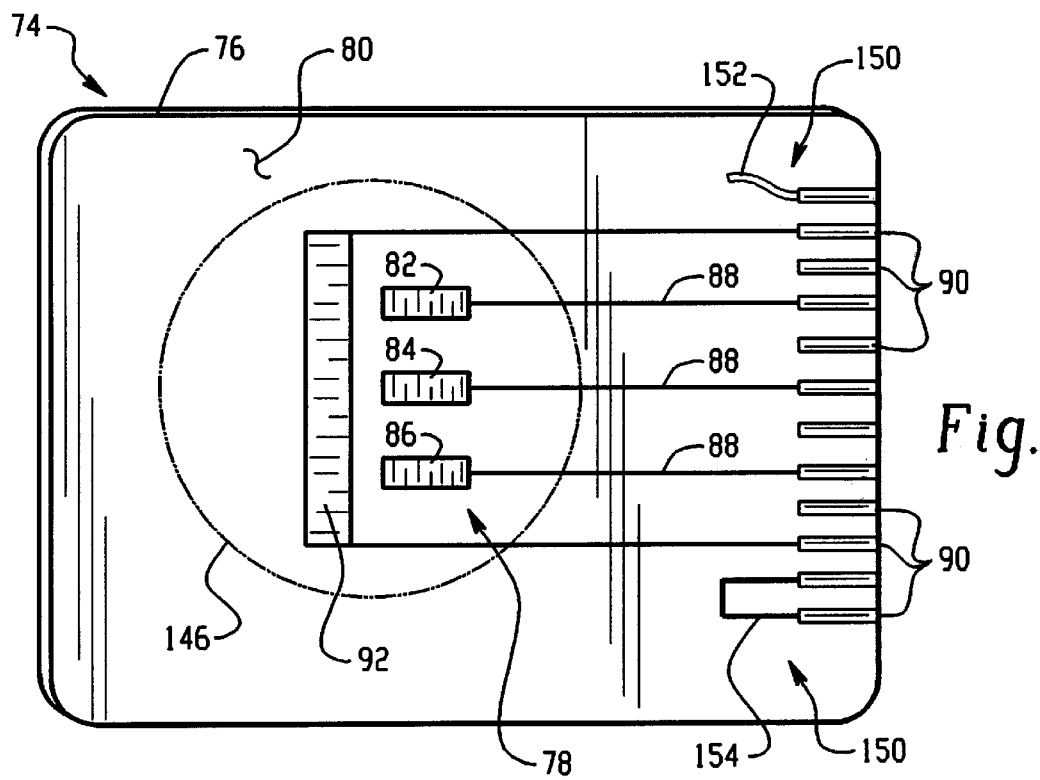
FIG. 3 is an enlarged front view of the sensor card of FIG. 2.

With reference also to FIGS. 2 and 3, the sensor system A includes a controller 70, and a sensor card support system 72. The sensor card support system receives a disposable sensor card 74 and holds the sensor card in contact with the circulating decontaminant solution.

The sensor card includes a substrate 76 formed from a sheet of a polymeric or ceramic support material, such as polyester, plastic, or other relatively inert material. A particularly preferred substrate material is polyester. Electrodes 78 are supported on a front face 80 of the substrate for electrochemical detection of the concentration of the decontaminant.

For detection of peracetic acid, in particular, the sensor card 74 preferably includes three electrodes 78, namely a working electrode 82, a reference electrode 84, and a counter electrode 86. A suitable reference electrode is a silver/silver chloride electrode. The working electrode is preferably a catalyst for peracetic acid. A particularly preferred working electrode includes gold, either alone, or doped with an inert material. Gold is an effective catalyst for peracetic acid and is selective for peracetic acid in the presence of hydrogen peroxide. The counter electrode is preferably formed from an inert conductive material, such as carbon, which readily accepts electrons. Alternatively, suitable counter electrodes are formed from silver, gold, or titanium.

Electric leads 88 electrically connect the electrodes and the controller 70 through connecting points 90. An insulation layer (not shown) partially covers the substrate and portions of the leads that would otherwise be exposed to the circulating decontaminant solution. The insulation layer exposes only a preselected area of each electrode to the solution and inhibits current from leaking into the solution from the leads. A thermistor 92 detects the temperature of the decontaminant solution in a region adjacent the sensor card.

Electrical components of the sensor card, including electrodes, electrical connection points, and electrical leads are all laid down on the front face of the substrate. This may be done by thin or thick film printing technology, or other conventional techniques. In one preferred method, materials for the electrodes and connection points are separately dispersed in inks and printed onto the substrate. The substrate is heated to evaporate solvents and set the inks. The sensor cards produced in this way are inexpensive and thus are suited to the intended single use.

The ink is selected so as to bond the electrode or lead to the substrate in such a way that it will not be disbanded when immersed in a peracetic acid solution at temperatures between around 25° C. and 75° C. The choice of ink also affects the conductivity to some degree.

Figure 4:
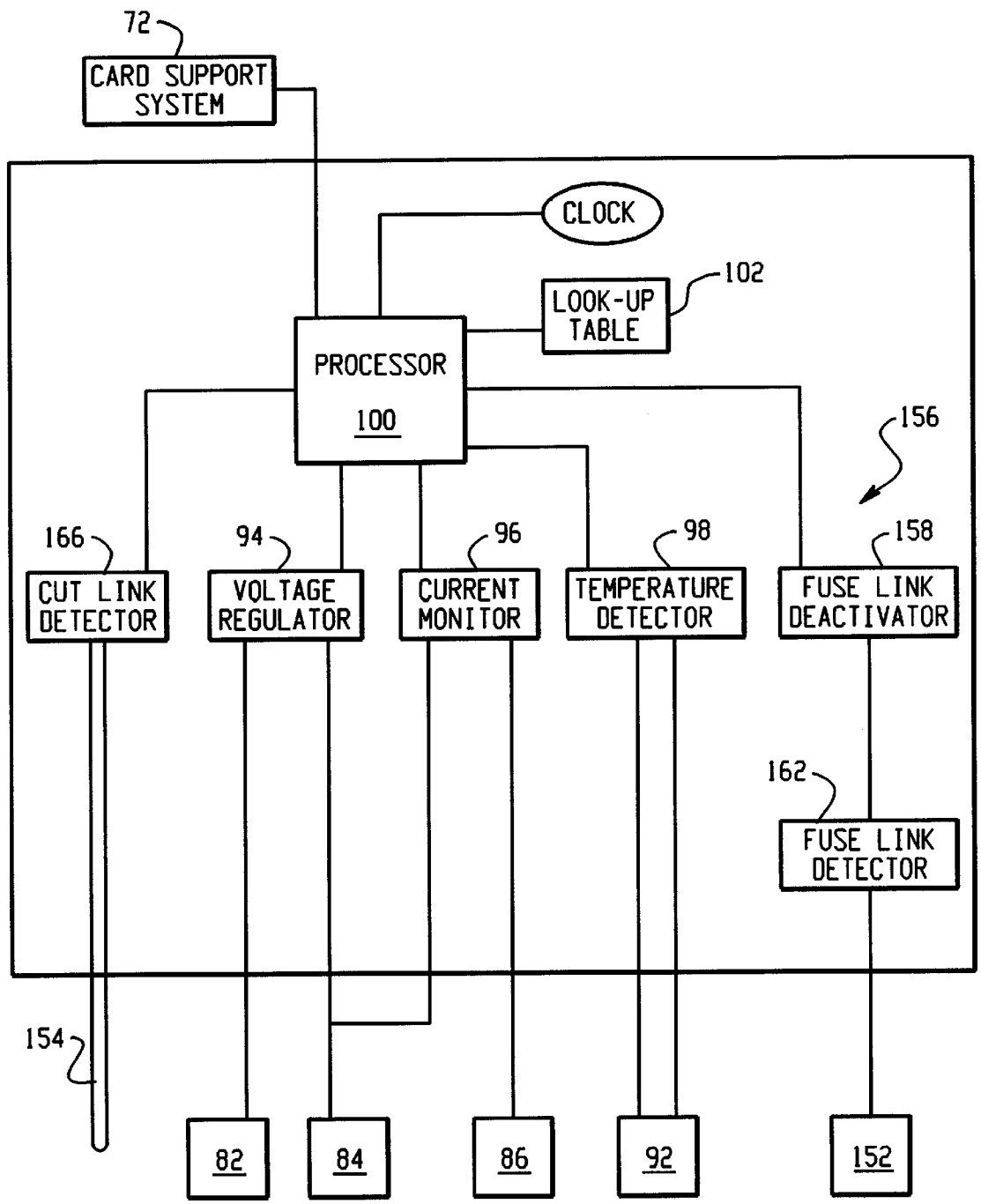
FIG. 4 is a schematic view of the controller of FIG. 1.

With reference also to FIG. 4, the controller 70 electrochemically monitors the peracetic acid concentration. Amperometric techniques are suited to the detection of peracetic acid. One suitable amperometric controller 70 is disclosed in PCT application WO 97/08544 and is incorporated herein by reference, although other conventional electrochemical monitoring systems may be used. In its simplest form, the controller includes a voltage regulator, such as a potentiostat 94 which maintains a constant voltage between the reference electrode 84 and the working electrode 82 and a current monitor 96 which detects the current flowing between the working electrode and the counter electrode 86. A temperature detector 98 receives temperature correction signals from the thermistor 92.

The voltage regulator, current monitor, and temperature detector are all controlled by a main processor 100. The main processor controls the voltage output of the voltage regulator 94 and receives current signals from the current monitor 96 and temperature signals from the temperature detector 98. The main processor accesses a look up table 102 to determine the concentration of peracetic acid. To load the look up table, samples of known concentration at known temperatures are measured and the monitored current noted. Due to the discrete intervals, an interpolator is optionally employed.

By repeating the measurements of current output and temperature over a period of time, at intervals of about 30 seconds, an accurate average measurement of the peracetic acid concentration in the flowing decontaminant solution is obtained. Preferably, the main processor 100 also controls the operation of the sensor card support system 72 and deactivation of the sensor card 74 to prevent reuse, as will be described in greater detail later.

Figure 5:
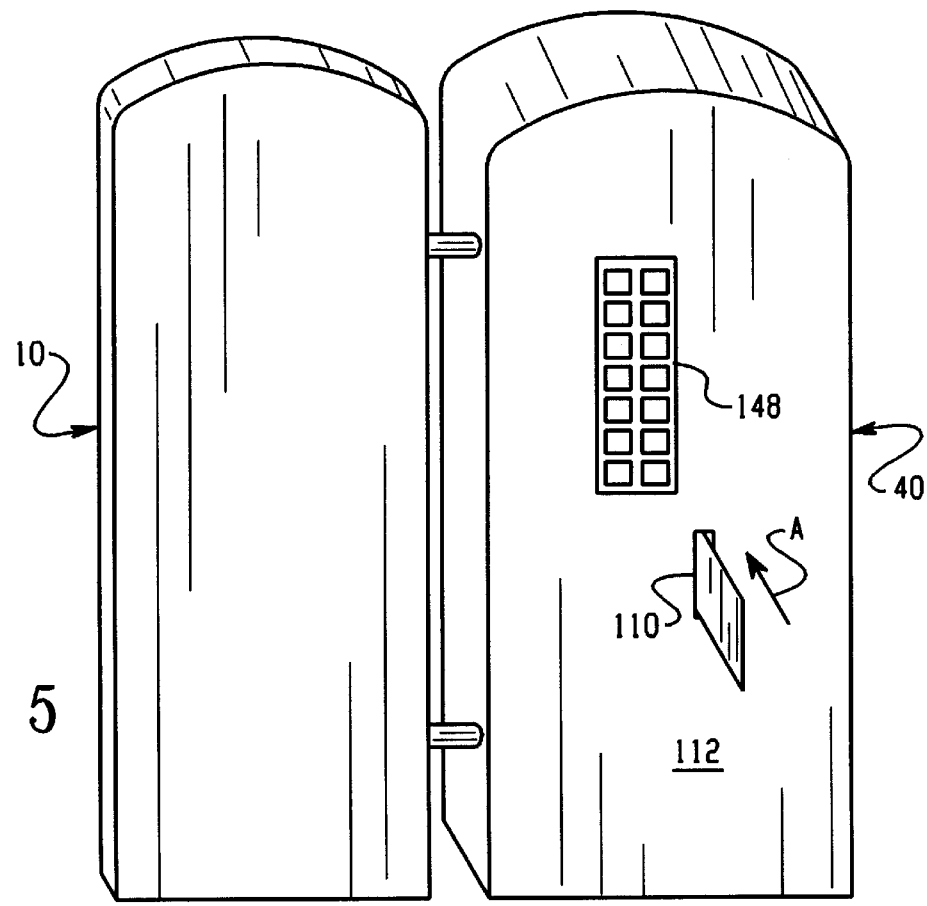
FIG. 5 is a front elevational view of the exterior of the decontamination system of FIG. 1.
Figure 6:
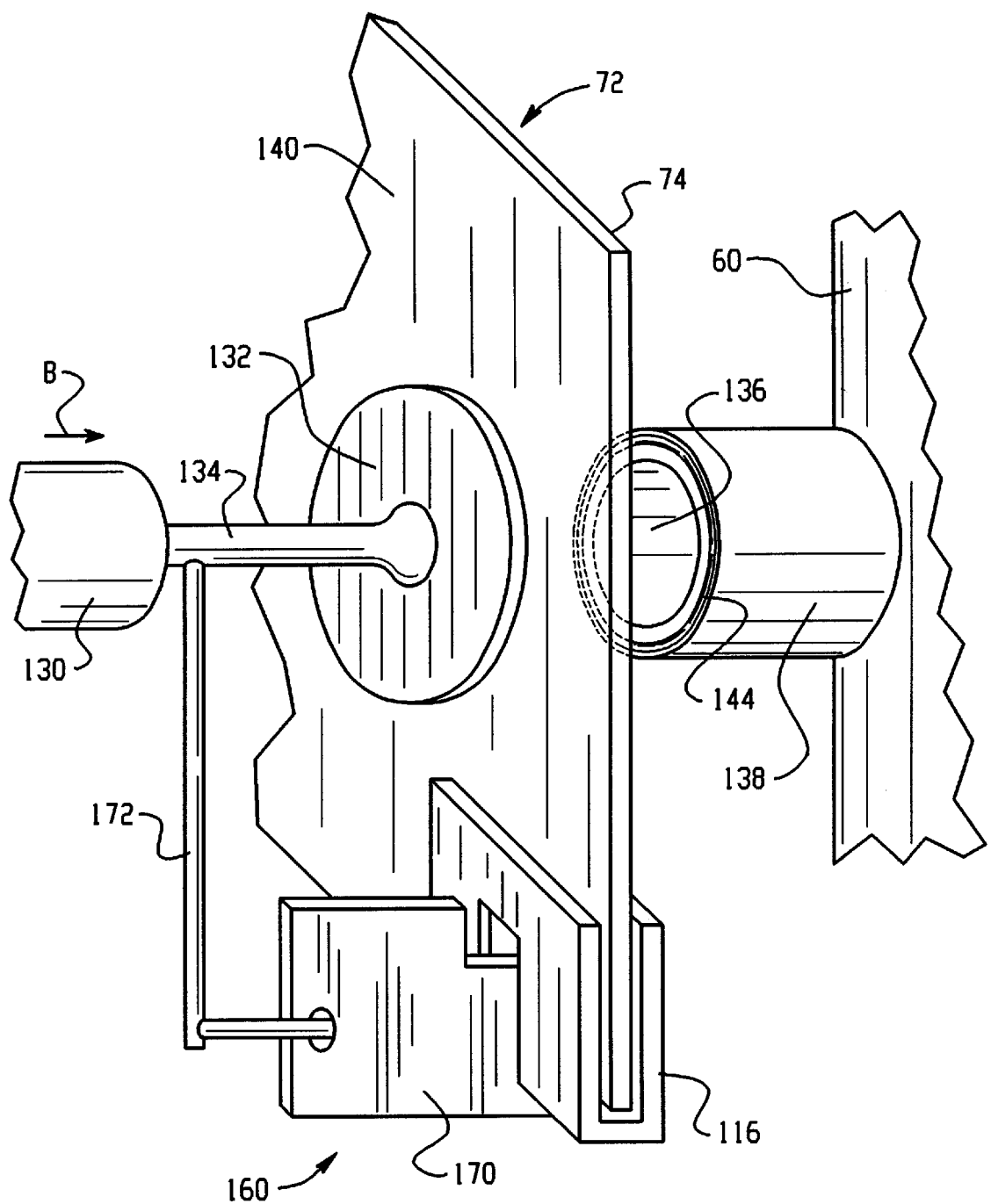
FIG. 6 is an enlarged perspective view of the rear face of sensor card and cut-link cutter according to the present invention.

With reference once more to FIG. 2 and reference also to FIGS. 5 and 6, the sensor card support system 72 positions the sensor card 74 so that the portion of the sensor card where the electrodes and thermistor are situated is disposed in fluid communication with the flowing decontaminant solution. The substrate is shaped like a credit card for insertion into a slot 110 in a front cover 112 of the supply cabinet 40. The sensor card is inserted into the slot in the direction of arrow A, as shown in FIG. 5.

Inside the supply cabinet 40, the sensor card 74 is received by upper and lower support channels 114 and 116 of the support system 72. The support channels loosely support upper and lower ends 118,120 of the sensor card 74 while permitting some movement of the sensor card in a direction perpendicular to the front face 80 of the sensor card.

Once inserted, the sensor card 74 is clamped in position in the slot, so that it cannot be removed during a decontamination cycle. Specifically, the sensor card support system 72 includes a ram, such as a pneumatic piston 130 which is attached to a clamping plate 132 by a piston rod 134. The support channels 114, 116 position the sensor card between the clamping plate and an opening 136 in a manifold 138 in the fluid line 60. The ram 130 is actuated by the controller 70 to apply a clamping force in the direction of arrow B. The force is delivered by the piston rod to the clamping plate and thence to a rear face 140 of the sensor card 74, as best shown in FIG. 6. The sensor card is pressed by the clamping plate 132 against the manifold 138. An O-ring 144, positioned around the opening 136 in the manifold, creates a seal between the front face 80 of the sensor card 74 and the manifold around the manifold opening when pressure is applied to the clamping plate 132.

A portion 146 of the sensor card where the electrodes 82, 84, 86 and thermistor 90 are located is thus positioned for contact with decontaminant solution that circulates through the manifold. Some of the decontaminant solution circulating through the fluid line 60 enters the manifold and contacts the electrodes.

Concentration measurements are made at intervals throughout the decontamination portion of a cycle and compared with preselected low concentration set points. The controller 70 signals the measured concentration to a display panel 148 on the front 112 of the supply cabinet 40. If the concentration of the decontaminant drops slightly below a preselected first operating concentration set point, the controller automatically extends the preprogrammed cycle by a corresponding time to compensate for the lower decontaminant concentration. If the concentration of the decontaminant falls below a second, lower minimum operating concentration set point the controller automatically ends the cycle and signals the display panel 148 to indicate a stoppage by visual or audible means, such as a flashing warning light or an alarm sound.

It should be appreciated that FIG. 2 exaggerates the distance between the manifold opening 136 and the clamping plate 132 for purposes of describing the features of the sensor card support system. In practice, the clamping plate and manifold opening are preferably separated by a relatively short distance, only slightly wider than the width of the sensor card.

The ram 130 maintains the pressure on the clamping plate 132 throughout the decontamination cycle. At the end of the cycle, the controller 70 signals the ram to release the pressure, allowing the sensor card 74 to be removed from the slot 110. Before releasing the sensor card, however, the sensor card is mutilated in a manner which is recognizable by the controller, to prevent reuse.

With reference once again to FIGS. 2 and 3, a preferred reuse-prevention system 150 is incorporated into the sensor card 74. The reuse prevention system includes two separate components, a fuse link 152 and a cut link or electrical line 154 which are separately deactivated by the sensor system to prevent reuse of the sensor card. The sensor system A includes a two-part reuse-prevention activation system 156 which selectively deactivates the fuse link and the cut link. The activation system 156 includes a fuse link deactivator 158, in the controller 70, and a cut link deactivator 160, within the sensor card support system 72.

The fuse link 152 is laid down on the sensor card 74 in a similar manner to the electrodes. The fuse link deactivator 158 is preferably operated by the main processor 100. At the end of a decontamination cycle, or if the power is switched off, the main processor 100 signals the fuse link deactivator 158 to send a brief burst or pulse of current through the fuse link, blowing the fuse. If the sensor card is subsequently reinserted into the slot 110 a fuse link detector 162 within the controller 70 recognizes the lack of electric continuity indicating that the link has been blown and prevents initiation of a new decontamination cycle until a fresh sensor card has been inserted.

The cut link 154 is laid down on the sensor card 74 adjacent one or other of the ends 118, 120 of the sensor card. The cut link completes a circuit with the controller 70. When the cut link is severed, the circuit is broken. Before initiating a sterilization cycle a cut link detector 166 within the controller tests the circuit through the cut link. The cut link also serves as a visual indication of whether the sensor card has been used.

Figure 7:
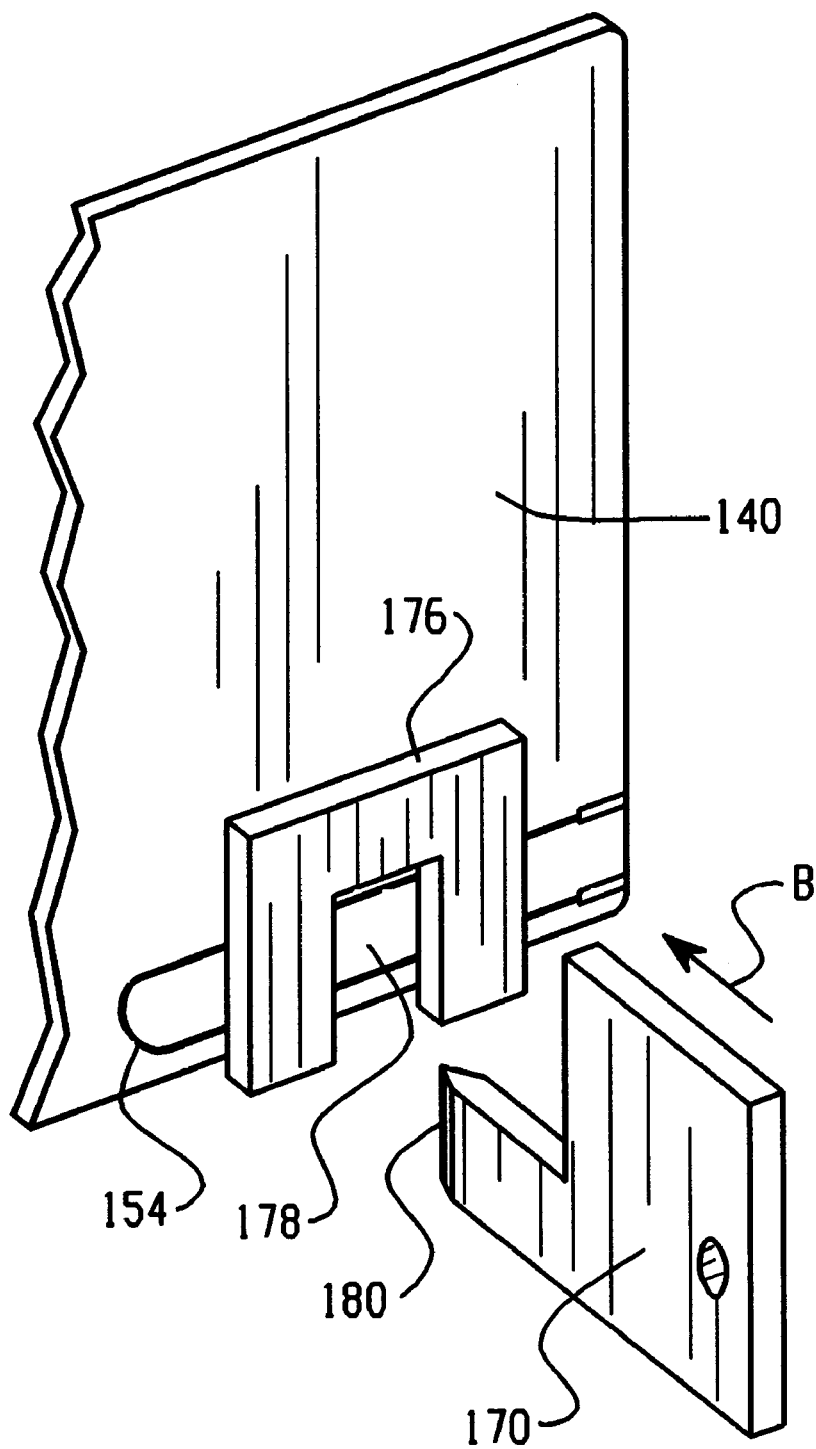
FIG. 7 is an enlarged perspective view of the sensor card, cutter and ram of the present invention; and, FIG. 8 is a flow diagram indicating the steps taken by the controller during a decontamination cycle.

With reference also to FIGS. 6 and 7, the cut link deactivator 160 includes a cutter 170 which severs the cut link 154. The cutter is preferably connected to the ram 130, such that when the ram is actuated by the controller 70, the cutter moves towards the rear face 140 of the sensor card in tandem with the clamping plate 132. As shown in FIG. 6 the cutter is optionally connected by a second rod 172 to the piston rod 134, although other methods of connecting the cutter to the ram are also contemplated, such as dual piston rods.

Although FIG. 7 shows the cut link 154 printed on the rear face 140 of the sensor card 74, it should be appreciated that the cut link may be laid down on either the front face or the rear face of the sensor card. For convenience, the cut link is preferably laid down on the front face of the sensor card at the same time as the electrodes, thermistor and fuse link, in a similar manner.

An anvil plate 176 firmly holds the end of the sensor card 74 adjacent the cut link 154. An opening 178 in the anvil plate provides access to the cut link and receives a cutting edge 180 of the cutter therethrough. The ram 130 forces the cutting edge through the opening and the sensor card, severing the cut link in the process. The cut link detector 166 within the controller recognizes that the link has been broken. The cutter 170 remains inserted through the sensor card until the pressure from the ram 130 is released. This inhibits removal of the sensor card during the sterilization cycle.

Accordingly, the cut link 154 is severed before the decontamination cycle commences. Although the cut link has been broken, the controller does not halt the decontamination cycle before it is completed unless power to the controller is prematurely switched off. Rather, the controller creates a "memory" of the previously detected validity of the cut link which is only destroyed at the end of a cycle or when the power is switched off. The memory overrides detection of the severing of the cut link. If the cycle is temporarily halted during the decontamination cycle, the memory is not lost and the controller allows the cycle to recontinue when the cycle is restarted. When the cycle is halted, the controller signals the display panel 148 to show a "ready" light, indicating that the cycle may be recommenced without inserting a fresh sensor card. If the memory is lost, the controller detects that the cut link has been severed, blows the fuse link 152, and signals the display panel 148 to switch the "ready" light off.

Alternately, the cutter 170 can cut other leads such as leads 82, at the end of the cycle. The cut link detector can be embodied in a logic circuit that detects then non-responsiveness of the sensor electrodes or the thermistor.

Figure 8:
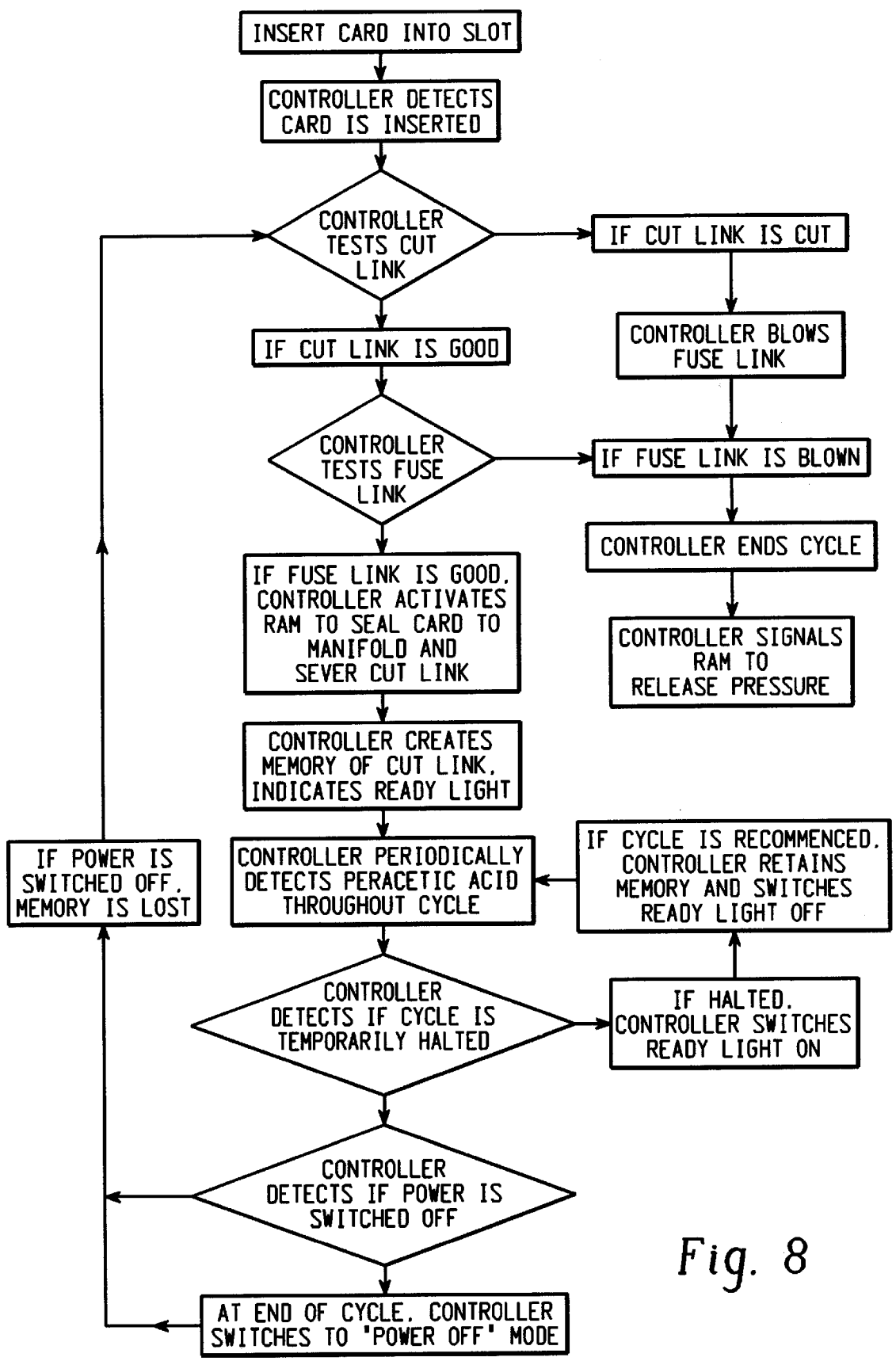

FIG. 8 summarizes a preferred sequence of steps taken by the controller during a typical decontamination cycle. The controller 70 detects that the sensor card 74 has been inserted into the slot and checks the fuse link 152 and cut link 154. If both of these are unbroken, the controller signals the display panel 148 to indicate a satisfactory test of the sensor card and actuates the ram 130. The controller recognizes that the cutter 170 has severed the cut link and creates a memory. If either of the cut link or the fuse link have been deactivated, however, the controller signals the display panel 148 to indicate that the sensor card should be replaced and halts the decontamination cycle until a fresh sensor card is inserted.

Once the memory has been created, the controller allows the decontamination cycle to commence and monitors the peracetic acid concentration periodically. If the cycle is halted temporarily, the controller 70 retains the memory, and switches the ready light on. If the cycle is recommenced, the controller continues peracetic acid detection. If the cycle is aborted, the controller switches to a "power off" mode. The memory is lost and the controller goes through the steps of blowing the fuse link 152 and disengaging the ram 130. If the cycle continues to completion, the controller switches to the power off mode and repeats the same sequence.

When the sensor card 74 is released by the ram 130, it is removed from the slot and may be stored together with a printout of the cycle to confirm that peracetic acid monitoring was carried out.

While the decontamination system has been described with particular reference to detection of peracetic acid, it should be appreciated that the system is also applicable to detection of hydrogen peroxide and other oxidizing and reducing species. By choosing counter and working electrodes which are particularly suited to the species to be detected, and appropriate electrochemical monitoring techniques, the system may be tailored to the specific detection of a variety of species.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment the invention is now claimed to be:

1. A decontamination system for sterilizing or disinfecting instruments with a decontaminant solution, the system including:
    a decontamination cabinet which defines a chamber for receiving the instruments to be decontaminated;
    a source of the decontaminant solution;
    a fluid line fluidly connecting the source of the decontaminant solution with the chamber;
    a sensor card support system for supporting a disposable sensor card in fluid communication with the fluid line, the sensor card including a plurality of electrodes and a reuse-prevention system; and
    a controller for detecting an electrical property of the electrodes and determining a concentration of a decontaminant in the decontaminant solution from the detected electrical property and for detecting whether the reuse-prevention system has been activated.

2. The system of claim 1, wherein the fluid line includes a manifold which defines an opening therein and wherein the sensor card support system includes:
    a ram,
    a clamping plate disposed between the ram and the sensor card, the ram for selectively applying a pressure to the clamping plate to seal the sensor card across the opening in the manifold such that the electrodes are in fluid contact with decontaminant solution entering the manifold.

3. The system of claim 2 wherein the reuse-prevention system includes a cuttable link and wherein the controller includes a cut link detector for detecting whether the cuttable link is severed and wherein the sensor card support system further includes:
    a cutter for severing the cuttable link.

4. The system of claim 3, wherein the sensor card support system includes an anvil plate for supporting the sensor card adjacent the cuttable link and for receiving the cutter therethrough.

5. The system of claim 1, wherein the reuse-prevention system includes a fuse link, and wherein the controller includes a fuse link detector for detecting whether the fuse link has been broken.

6. The system of claim 1, wherein the fluid line and the chamber define a recirculation loop which recirculates decontaminant solution through the chamber and wherein the sensor card support system supports the sensor card in fluid communication with decontaminant solution that has passed through the chamber.

7. The system of claim 1, wherein the sensor card includes a substrate and wherein the electrodes are disposed on a surface of the substrate.

8. The system of claim 1, wherein the source of the decontaminant solution is a well which receives a container of concentrated decontaminant solution, the system further including:
    a water inlet line for delivering diluting water to the well for diluting the concentrated decontaminant solution; and,
    a microporous filter in the fluid inlet line for filtering out particles of dirt and microorganisms.

9. A sensor system for detecting a concentration of a component of a liquid disposed in a liquid treatment system, the sensor system comprising:
    a sensor card support system for supporting a disposable sensor card in fluid communication with the liquid in the liquid treatment system, the sensor card including a plurality of electrodes and a reuse-prevention system;
    a controller for establishing electrical contact with the electrodes for electrochemically measuring an electrical property of the electrodes which is dependent on the concentration of the component in the liquid;
    a reuse-prevention activation system for activating the reuse prevention system; and,
    a detector for detecting an activation of the reuse-prevention system.

10. The sensor system of claim 9, further including a manifold in fluid communication with the liquid treatment system, the manifold defining an opening therein, and wherein the sensor card support system includes:

a ram, a clamping plate disposed between the ram and the sensor card, the ram for selectively applying a pressure to the clamping plate to seal the sensor card across the opening in the manifold such that the electrodes are in fluid contact with the liquid entering the manifold.

11. The system of claim 10 wherein the reuse-prevention system includes an electrical link on the card and wherein the controller includes a cut link detector for detecting whether the electrical link is severed and wherein the reuse-prevention activation system includes:

a cutter connected to the ram, the ram selectively applying pressure to the cutter for severing the electrical link.

12. The system of claim 11, wherein the clamping plate and the cutter are connected to the ram through a common piston rod such that the cutter cuts the electrical link when the clamping plate seals the sensor card across the opening.

13. The system of claim 11, wherein the sensor card support system includes an anvil plate, the anvil plate for supporting the sensor card adjacent the electrical link and for receiving the cutter therethrough.

14. The system of claim 10, wherein the reuse-prevention system includes a fuse link, and wherein the controller includes:

a fuse link detector for detecting whether the fuse link has been broken; and, a fuse link deactivator for selectively blowing the fuse link.

15. A method of preventing reuse of a disposable sensor card for detecting the concentration of a decontaminant in a decontaminant solution, the sensor card including a plurality of electrodes and a reuse-prevention system, the method comprising:

determining whether the reuse-prevention system on the sensor card has been activated; and, if the reuse-prevention system has not been activated,
clamping the sensor card such that the electrodes are in contact with the decontaminant solution,
sensing an electrical property of the electrodes which is dependent on the concentration of a decontaminant in a decontaminant solution, and
activating the reuse-prevention system.

16. The method of claim 15, wherein the reuse prevention system includes a fuse link and wherein the step of activating the reuse-prevention system includes:

blowing the fuse link when a preselected event occurs, and wherein the step of determining whether the reuse-prevention system on the sensor card has been activated includes:
detecting whether the fuse link has been blown.

17. The method of claim 16, wherein the preselected event is the completion of a decontamination process.

18. The method of claim 15, wherein the sensor card includes an electrical line and the step of activating the reuse prevention system includes:

severing the electrical line;

and wherein the step of determining whether the reuse-prevention system on the sensor card has been activated includes:
detecting whether the electrical line has been severed.

19. A method of decontamination of items with a decontaminant solution, the method comprising:

disposing the items to be decontaminated in a chamber;

determining whether a reuse-prevention system on a disposable sensor card has been activated, the sensor card including a plurality of electrodes; and, if the reuse-prevention system has not been activated,
clamping the sensor card such that the electrodes are in contact with the decontaminant solution,
sensing an electrical property of the electrodes which is dependent on the concentration of a decontaminant in the decontaminant solution, a
contacting the items with the decontaminant solution for a period sufficient to effect decontamination,
activating the reuse-prevention system, and
unclamping the sensor card.

20. The method of claim 19, wherein the step of clamping includes:

clamping the sensor card across an opening in a fluid line which recirculates the decontaminant solution through the chamber such that the electrodes are in contact with the recirculating decontaminant solution.

21. The method of claim 19, wherein the re-use prevention system includes a cut link and wherein step of activating the reuse-prevention system includes:

severing the cut link during the step of clamping the sensor card;

and wherein the step of determining whether the reuse-prevention system on the sensor card has been activated includes:
determining whether the cut link has been severed.

22. The method of claim 21, wherein the method further includes after the step of severing the cut link:

creating a memory of the cut link in a controller which overrides detection of whether the reuse-prevention system on the sensor card has been activated unless power to the controller is interrupted;

if power to the controller is interrupted and recommenced, repeating the step of determining whether the reuse-prevention system on the sensor card has been activated.

* * * * *